(12) United States Patent
Kelly et al.

(10) Patent No.: US 7,345,074 B2
(45) Date of Patent: Mar. 18, 2008

(54) DERIVATIVES OF [6,7-DIHYDRO-5H-IMIDAZOL[1,2-A] IMIDAZOLE-3-SULFONYLAMINO]-PROPIONAMIDE

(75) Inventors: Terence Alfred Kelly, Ridgefield, CT (US); Jin Mi Kim, Sandy Hook, CT (US); René Marc Lemieux, Plantsville, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 171 days.

(21) Appl. No.: 10/969,105

(22) Filed: Oct. 20, 2004

(65) Prior Publication Data

US 2005/0054703 A1   Mar. 10, 2005

Related U.S. Application Data

(62) Division of application No. 10/686,073, filed on Oct. 15, 2003, now Pat. No. 6,844,360.

(60) Provisional application No. 60/422,446, filed on Oct. 30, 2002.

(51) Int. Cl.
  *A61K 31/4166* (2006.01)
  *C07D 235/02* (2006.01)
  *C07D 403/02* (2006.01)

(52) U.S. Cl. .................. 514/387; 548/302.7
(58) Field of Classification Search ................ 514/387; 548/302.7
See application file for complete search history.

(56) References Cited

U.S. PATENT DOCUMENTS

| 6,355,664 | B1 | 3/2002 | Kelly et al. |
| 6,437,148 | B1 | 8/2002 | Frutos et al. |
| 6,492,408 | B1 | 12/2002 | Wu et al. |
| 6,689,804 | B2 | 2/2004 | Wu |
| 6,844,360 | B2 | 1/2005 | Kelly |

FOREIGN PATENT DOCUMENTS

| WO | WO 98/39303 A1 | 9/1998 |
| WO | WO 01/07440 A1 | 2/2001 |

OTHER PUBLICATIONS

Springer, T. A.; "Adhesion receptors of the immune system"; Nature, 1990, 346, pp. 425-434.
Kishimoto, T. K. et al; "Integrins, ICAMs, and Selectins: Role and Regulation of Adhesion Molecules in Neutrophil Recruitment to Inflammatory Sites"; Adv. Pharmacol. 1994, 25, pp. 117-138.
Diamond, M.S.; "The dynamic regulation of integrin adhesiveness"; Current Biology, 1994, 4, pp. 506-517.
Anderson, D.C. et al; "Leukocyte LFA-1, OKM1, p150,95 deficiency syndrome: functional and biosynthetic studies of three kindreds1,2"; Fed. Proc. 1985, 44, pp. 2671-2677.
Anderson, D.C. et al; "The Severe and Moderate Phenotypes of Heritable Mac-1,LFA-1 Deficiency: Their Quantitative Definition and Relation to Leukocyte Dysfunction and Clinical Features"; J Infect Dis., 1985, 152, pp. 668-689.
Gorski, A.; "The role of cell adhesion molecules in immunopathology"; Immunology Today, 1994, 15, pp. 251-255.
Rothlein, R. et al; "1. Leukocyte Adhesion in Inflammation: From Discovery to the Clinic"; Adhesion Molecules; Wegner, C. D., ed.; 1994, pp. 1-8.
Cosimi, A.B. et al; "In Vivo Effects Of Monoclonal Antibody To ICAM-1 (CD54) In Nonhuman Primates With Renal Allografts1"; J. Immunol. 1990, 144, pp. 4604-4612.
Kavanaugh, A. F. et al; "Treatment of Refractory Rheumatoid Arthritis With A Monoclonal Antibody To Intercellular Adhesion Molecule 1"; Arthritis Rheum. 1994, 37, pp. 992-1004.
Fischer, A. et al; "Prevention of Graft Failure By An Anti-HLFA-1 Monoclonal Antibody In HLA-Mismatched Bone-Marrow Transplantation"; Lancet, 1989, 2, pp. 1058-1060.
LeMauff, B. et al; "Effect of Anti-LFA1 (CD11a) Monoclonal Antibodies In Acute Rejection In Human Kidney Transplantation"; Transplantation, 1991, 52, pp. 291-295.
Becker, J. C. et al; "Soluble Intercellular Adhesion Molecule-1 Inhibits MHC-Restricted Specific T Cell/Tumor Interation"; J. Immunol., 1993, 151, pp. 7224-7232.
Roep, B. O., et al; "Soluble forms of intercellular adhesion molecule-1 in insulin-dependent diabetes mellitus"; Lancet, 1994, 343, pp. 1590-1593.
Bowcock, et al; Getting Under the Skin: The Immunogenetics of Psoriasis; Nature Reviews Immunology; Sep. 2005; vol. 5; pp. 699-711; Nature Publishing Group.
Gottlieb; Psoriasis: Emerging Therapeutic Strategies; Nature Review Drug Discovery; Jan. 2005; vol. 4; pp. 19-34.
Kelly, et al; Cutting Edge: A Small Molecule Antagonist of LFA-1-Mediated Cell Adhesion; The Journal of Immunology; 1999; vol. 163; pp. 5173-5177.
Last-Barney, et al; Binding Site Elucidation of Hydantoin-Based Antagonists of LFA-1 Using Multidisciplinary Technologies: Evidence for the Allosteric Inhibition of a Protein-Protein Interaction; Journal of American Chemical Society; 2001; vol. 123; pp. 5643-5650.
Wu, et al; Second-Generation Lymphocyte Function-Associated Antigen-1 Inhibitors: 1H-Imidazol[1,2-a]imidazol-2-one Derivatives; Journal of Medicinal Chemistry; 2004; vol. 47; pp. 5356-5366.

*Primary Examiner*—Sreeni Padmanabhan
*Assistant Examiner*—Yong S. Chong
(74) *Attorney, Agent, or Firm*—Michael P. Morris; Mary-Ellen M. Devlin; Philip I. Datlow

(57) ABSTRACT

Derivatives of [6,7-dihydro-5H-imidazo[1,2-a]imidazole-3-sulfonylamino]-propionamide which exhibit good inhibitory effect upon the interaction of CAMs and Leukointegrins and are thus useful in the treatment of inflammatory disease.

4 Claims, No Drawings

DERIVATIVES OF [6,7-DIHYDRO-5H-IMIDAZOL[1,2-A] IMIDAZOLE-3-SULFONYLAMINO]-PROPIONAMIDE

CROSS-REFERENCE TO RELATED APPLICATIONS

This application is a divisional of U.S. application Ser. No. 10/686,073, filed Oct. 15, 2003 now U.S. Pat. No. 6,844,360, which claims the benefit of U.S. Provisional Application Ser. No. 60/422,446, filed Oct. 30, 2002, and said applications are herein incorporated by reference.

BACKGROUND OF THE INVENTION

1. Technical Field

The present invention relates generally to a class of derivatives of [6,7-dihydro-5H-imidazo[1,2-a]imidazole-3-sulfonylamino]-propionamide, the synthesis of these compounds, their use in the treatment of inflammatory disease, and pharmaceutical compositions comprising these compounds.

2. Background Information

Research spanning the last decade has helped to elucidate the molecular events attending cell-cell interactions in the body, especially those events involved in the movement and activation of cells in the immune system. See generally, Springer, T. *Nature*, 1990, 346, 425-434. Cell surface proteins, and especially the Cellular Adhesion Molecules ("CAMs") and "Leukointegrins", including LFA-1, MAC-1 and gp150.95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently believed that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2, ICAM-3 or ICAM-4 which are expressed on blood vessel endothelial cell surfaces and on other leukocytes. The interaction of the CAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally Kishimoto, T. K.; Rothlein; R. R. *Adv. Pharmacol.* 1994, 25, 117-138 and Diamond, M.; Springer, T. *Current Biology*, 1994, 4, 506-517.

A group of individuals has been identified which lack the appropriate expression of Leukointegrins, a condition termed "Leukocyte Adhesion Deficiency" (Anderson, D. C.; et al., *Fed. Proc.* 1985, 44, 2671-2677 and Anderson, D. C.; et al., *J. Infect. Dis.* 1985, 152, 668-689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD18 family. By virtue of the fact that LAD patients who lack CD18 cannot mount an inflammatory response, it is believed that antagonism of CD18, CD11/ICAM interactions will also inhibit an inflammatory response.

It has been demonstrated that the antagonism of the interaction between the CAMs and the Leukointegrins can be realized by agents directed against either component. Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to CAMs or Leukointegrins include antigen or mitogen-induced lymphocyte proliferation, homotypic aggregation of lymphocytes, T-cell mediated cytolysis and antigen-specific induced tolerance. The relevance of the in vitro studies are supported by in vivo studies with antibodies directed against ICAM-1 or LFA-1. For example, antibodies directed against LFA-1 can prevent thyroid graft rejection and prolong heart allograft survival in mice (Gorski, A.; *Immunology Today*, 1994, 15, 251-255). Of greater significance, antibodies directed against ICAM-1 have shown efficacy in vivo as anti-inflammatory agents in human diseases such as renal allograft rejection and rheumatoid arthritis (Rothlein, R. R.; Scharschmidt, L., in: *Adhesion Molecules*, Wegner, C. D., Ed., 1994, 1-8; Cosimi, C. B., et al., *J. Immunol.* 1990, 144, 4604-4612 and Kavanaugh, A. et al., *Arthritis Rheum.* 1994, 37, 992-1004) and antibodies directed against LFA-1 have demonstrated immunosuppressive effects in bone marrow transplantation and in the prevention of early rejection of renal allografts (Fischer, A.; et al., *Lancet*, 1989, 2, 1058-1060 and Le Mauff, B.; et al., *Transplantation*, 1991, 52, 291-295).

It has also been demonstrated that a recombinant soluble form of ICAM-1 can act as an inhibitor of the ICAM-1 interaction with LFA-1. Soluble ICAM-1 acts as a direct antagonist of CD18,CD11/ICAM-1 interactions on cells and shows inhibitory activity in in vitro models of immune response such as the human mixed lymphocyte response, cytotoxic T cell responses and T cell proliferation from diabetic patients in response to islet cells (Becker, J. C.; et al., *J. Immunol.* 1993, 151, 7224 and Roep, B. O.; et al., *Lancet*, 1994, 343, 1590).

Thus, the prior art has demonstrated that large protein molecules which antagonize the binding of the CAMs to the Leukointegrins have therapeutic potential in mitigating inflammatory and immunological responses often associated with the pathogenesis of many autoimmune or inflammatory diseases. However proteins have significant deficiencies as therapeutic agents, including the inability to be delivered orally and potential immunoreactivity which limits the utility of theses molecules for chronic administration. Furthermore, protein-based therapeutics are generally expensive to produce.

It follows that small molecules having the similar ability as large protein molecules to directly and selectively antagonize the binding of the CAMs to the Leukointegrins would make preferable therapeutic agents.

Several small molecules have been described in the literature that affect the interaction of CAMs and Leukointegrins. For example, U.S. Pat. No. 6,355,664 and the corresponding WO 98/39303 disclose a class of small molecule, having a hydantoin core, that are inhibitors of the interaction of LFA-1 and ICAM-1. Of greater relevance to the present invention is WO 01/07440 A1, which discloses compounds that instead have an 6,7-dihydro-5H-imidazo[1, 2-a]imidazole core. While the compounds that are specifically described by WO 01/07440 A1 have a more potent inhibitory affect upon the interaction of CAMs and Leukointegrins than do the hydantoins of U.S. Pat. No. 6,355,664 and the corresponding WO9839303, they nevertheless are not ideal therapeutic agents because the rate at which they are metabolized is undesirably high.

Thus, the problem to be solved by the present invention is to find small molecules that have not only good inhibitory effect upon the interaction of CAMs and Leukointegrins but that also are metabolized at a rate that is not overly rapid.

BRIEF SUMMARY OF THE INVENTION

The invention is a subset or selection of the 6,7-dihydro-5H-imidazo[1,2-a]imidazoles that are generically but not specifically described by WO 01/07440 A1. Quite surprisingly, the compounds included within the invention exhibit not only good inhibitory effect upon the interaction of CAMs and Leukointegrins but are metabolized much more slowly than are the compounds that are specifically described by WO 01/07440 A1. The compounds of the invention solve the problem of overly rapid metabolism.

DETAILED DESCRIPTION OF THE INVENTION

The invention comprises compounds of the formula I

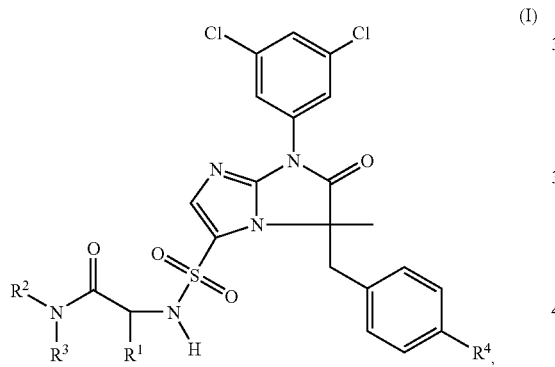

wherein:
$R^1$ is straight or branched alkyl of 1 to 3 carbon atoms which is optionally mono- or disubstituted with moieties independently selected from the group consisting of:
  (i) oxo and
  (ii) morpholino;
$R^2$ and $R^3$ are each, independently selected from the group consisting of:
  (A) hydrogen, and
  (B) straight or branched alkyl of 1 to 4 carbon atoms which alkyl group is mono- or disubstituted with moieties independently selected from the group consisting of:
    (i) $CONH_2$ and
    (ii) OH,
or $R^2$ and $R^3$ together with the nitrogen atom between them form a piperazine ring; and
$R^4$ is:
  (A) cyano,
  (B) pyrimidine which is mono- or disubstituted with $NH_2$ or
  (C) trifluoromethoxy.

Preferred compounds of the invention are those of the formula I, wherein:
$R^1$ is a methyl group;
$R^2$ and $R^3$ are each, independently selected from the group consisting of:
  (A) hydrogen and
  (B) straight or branched alkyl of 1 to 4 carbon atoms which is mono- or disubstituted with moieties independently selected from the group consisting of:
    (i) $CONH_2$ and
    (ii) OH; and
$R^4$ is:
  (A) cyano or
  (B) trifluoromethoxy.

More preferred are compounds of the formula I wherein:
$R^1$ is a methyl group;
$R^2$ and $R^3$ are each, independently selected from the group consisting of:
  (A) hydrogen and
  (B) straight or branched alkyl of 1 to 4 carbon atoms which is mono- or disubstituted with moieties independently selected from the group consisting of:
    (i) $CONH_2$ and
    (ii) OH; and
$R^4$ is trifluoromethoxy.

It will be appreciated that the compounds of the formula I have at least two chiral centers. In an ultimately preferred generic aspect, the invention includes compounds of formula I with the absolute stereochemistry depicted below in formula I*.

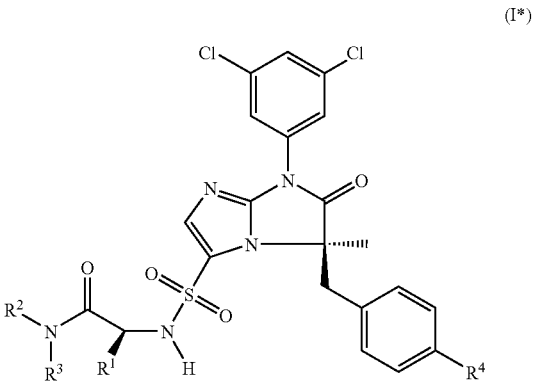

Specifically preferred are compounds of the formula I selected from the group consisting of:
(S)-2-[(R)-5-(4-Cyano-benzyl)-7-(3,5-dichloro-phenyl)-5-methyl-6-oxo-6,7-dihydro-5H-imidazo[1,2-a]imidazole-3-sulfonylamino]-propionamide;
(S)-2-[(R)-7-(3,5-Dichloro-phenyl)-5-methyl-6-oxo-5-(4-trifluoromethoxy-benzyl)-6,7-dihydro-5H-imidazo[1,2-a]imidazole-3-sulfonylamino]-N-(2-hydroxy-2-methyl-propyl)-propionamide; (S)-2-[(R)-7-(3,5-Dichloro-phenyl)-5-methyl-6-oxo-5-(4-trifluoromethoxy-benzyl)-6,7-dihydro-5H-imidazo[1,2-a]imidazole-3-sulfonylamino]-propionamide; and (S)-N-Carbamoylmethyl-2-[(R)-5-(4-cyano-benzyl)-7-(3,5-dichloro-phenyl)-5-methyl-6-oxo-6,7-dihydro-5H-imidazo[1,2-a]imidazole-3-sulfonylamino]-propionamide.

The invention also includes pharmaceutically acceptable salts of the compounds of the formula I.

General Synthetic Methods

Compounds of the invention may be prepared by the general methods described below. Typically, reaction progress may be monitored by thin layer chromatography (TLC) if desired. If desired, intermediates and products may be purified by chromatography on silica gel and/or recrystallization, and characterized by one or more of the following techniques: NMR, mass spectroscopy and melting point. Starting materials and reagents are either commercially available or may be prepared by one skilled in the art using methods described in the chemical literature.

Compounds of formula I may be prepared from intermediate II. The synthesis of intermediate II is reported by Wu et al., U.S. Non-provisional application Ser. No. 09/604,312 and Frutos et al., U.S. Pat. No. 6,441,183, both incorporated herein by reference.

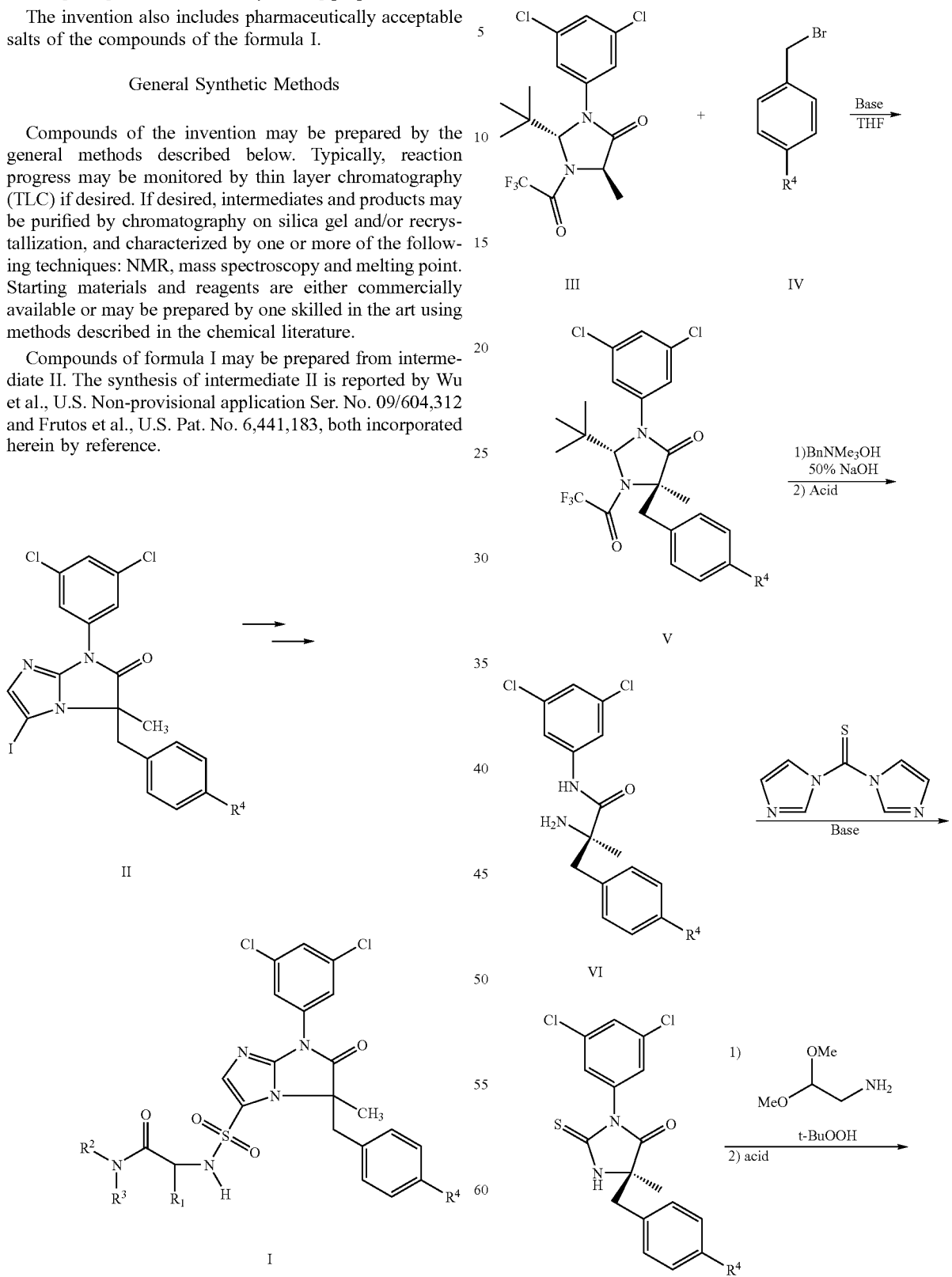

Intermediate II may be prepared by the procedure illustrated in Scheme I.

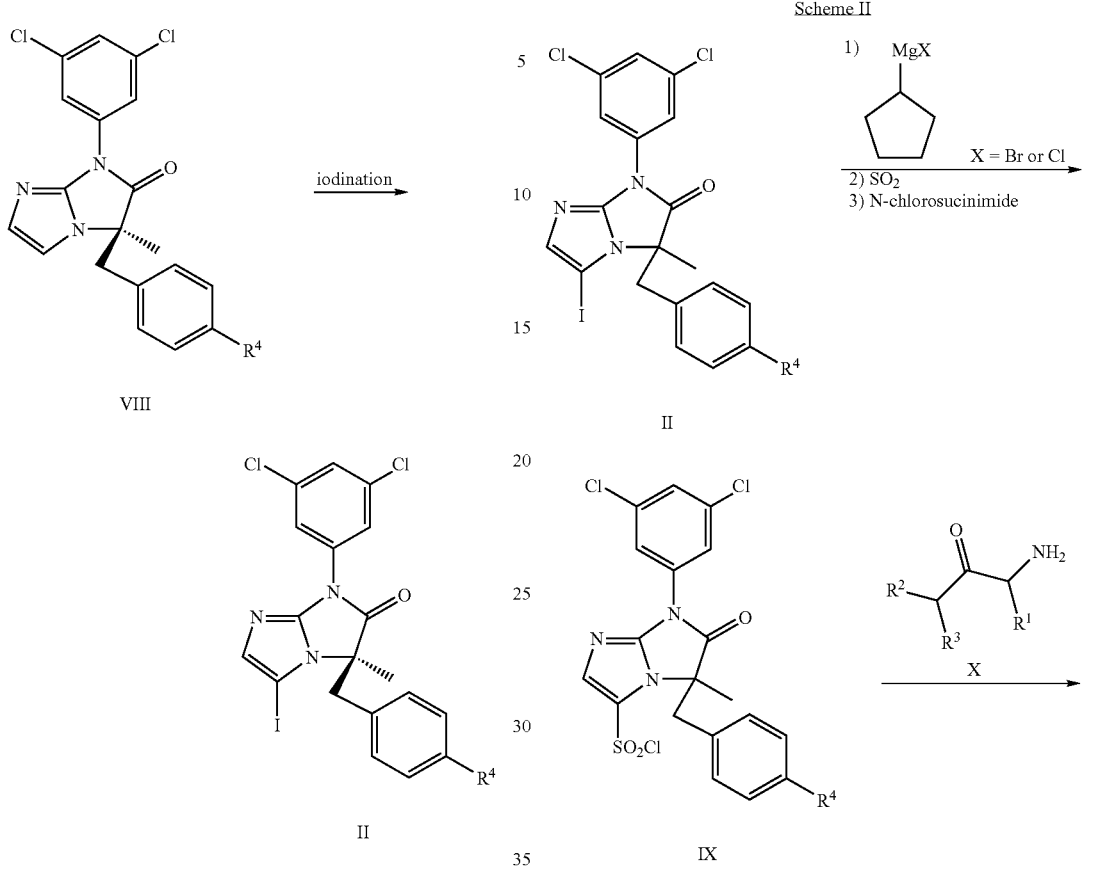

As illustrated above, intermediate III is deprotonated with a suitable base such as lithium bis(trimethylsilyl)amide at about −20° C. to −30° C., and then alkylated with a substituted benzyl halide, preferably a benzyl bromide (IV) to produce V. Hydrolysis of the trifluoroacetamide group of V, for example by treatment with 40% aqueous benzyltrimethylammonium hydroxide in dioxane/50% NaOH, followed by treatment with acid, such as HCl, provides VI. Treatment of VI with thiocarbonyldiimidazole in the presence of a base such as 4-(N,N-dimethylamino)pyridine provides VII. Treatment of VII with aminoacetaldehyde dimethyacetal and t-butylhydroperoxide solution, followed by treatment of the intermediate acetal with an acid such as p-toluenesulfonic acid provides VIII. Iodination of VIII by treatment with an iodinating agent such as N-iodosuccinamide provides II.

The method used for preparation of intermediate III, treatment of the amide formed from N-Boc-D-alanine and 3,5-dichloroaniline with trifluoroacetic acid to remove the Boc-group, followed by treatment with pivalaldehyde, and acylation of the resulting imidazolodone with trifluoroacetic anhydride is described in U.S. Pat. No. 6,414,161, cited above, and in the chemical literature (N. Yee, Org Lett., 2000, 2, 2781).

The synthesis of compounds of formula I from intermediate II is illustrated in Scheme II.

As illustrated above, treatment of II with a Grignard reagent, such as cyclopentyl magnesium bromide or chloride, followed by treatment of the resulting magnesium salt with $SO_2$ and then N-chlorosuccinimide provides the sulfonyl chloride IX. Treatment of IX with the desired amine (X) in the presence of a suitable base such as triethylamine, provides the desired product of formula (I). Intermediates X are either commercially available or readily prepared from commercially available starting materials by methods known in the art. The initial product of formula I may be further modified by methods known in the art to provide additional compounds of the invention. Several examples are provided in the Synthetic Examples section.

The desired $R^4$ on formula I compounds may be obtained by selection of the appropriately substituted intermediate IV in Scheme I. Alternately, intermediate VIII having $R^4$ being Br (VIIIa) may be converted to intermediates having $R^4$ being CN or a substituted 5-pyrimidyl group as illustrated in Scheme III.

dures described in Schemes I and II. The Suzuki reaction to convert $R^4$=Br to $R^4$=an optionally substituted pyrimidine may also be carried out on a compound of formula I. The Suzuki reaction may also be carried out in the reverse manner. The bromide VIIIa (or a compound of formula I with $R^4$=Br) may be converted to a boronate ester for example by treatment with bis(pinacolato)diboron in the presence of a palladium catalyst such as $PdCl_2$(dppf) and then reacted with the desired pyrimidyl bromide.

The invention is further described by the following synthetic examples.

SYNTHETIC EXAMPLES

Example 1

Synthesis of (R)-5-(4-bromo-benzyl)-7-(3,5-dichloro-phenyl)-5-methyl-6-oxo-6,7-dihydro-5H-imidazo[1,2-a]imidazole-3-sulfonyl chloride

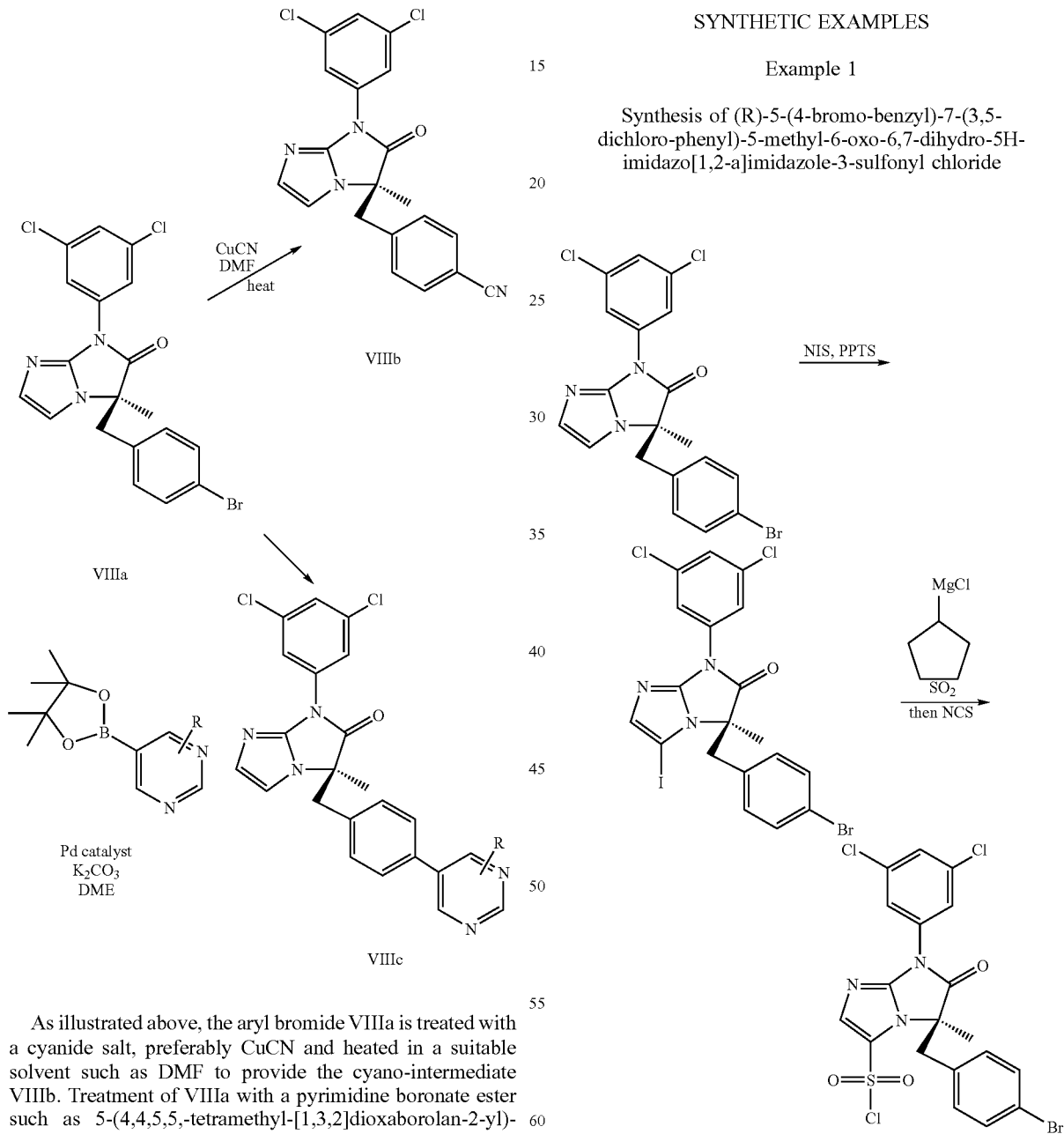

As illustrated above, the aryl bromide VIIIa is treated with a cyanide salt, preferably CuCN and heated in a suitable solvent such as DMF to provide the cyano-intermediate VIIIb. Treatment of VIIIa with a pyrimidine boronate ester such as 5-(4,4,5,5,-tetramethyl-[1,3,2]dioxaborolan-2-yl)-pyrimidine in the presence of a palladium catalyst such as [1,1'-bis(diphenylphosphino)ferrocene]dichloropalladium (II)•$CH_2Cl_2$ ($PdCl_2$(dppf)•$CH_2Cl_2$) and a base such as potassium carbonate in a suitable solvent (Suzuki reaction), for example dimethoxyethane, provides the pyrimidine intermediate VIIIc. Intermediates VIIIb and VIIIc may then be converted to desired compounds of formula I by the proce- A solution of (R)-3-(4-bromo-benzyl)-1-(3,5-dichloro-phenyl)-3-methyl-1H-imidazo[1,2-a]imidazol-2-one in THF (0.12M) was treated with N-iodosuccinimide (1.05 equiv) and pyridinium p-toluenesulfonate (0.1 equiv). The mixture was stirred at room temperature for 17 h, then diluted with EtOAc and washed with 10% $Na_2S_2O_3$ solution and water. The combined aqueous layers were extracted with EtOAc. The combined organic phases were washed with brine, dried over $Na_2SO_4$, filtered and concentrated. The crude oil was purified by silica gel chromatography to provide the desired iodide.

A solution of the above iodide in THF (0.12M) was cooled at −40° C. as c-pentyl magnesium chloride (1.05 equiv) was added dropwise over 10 min. After stirring at −40° C. for 1 h, $SO_2$ (g) was added by placing an inlet needle just above the surface of the reaction mixture for 1.5 min. The bright yellow mixture was warmed to −20° C. over 1 h and then stirred at room temperature for 1 h. $N_2$ (g) was bubbled through the mixture for 20 min followed by concentration and pumping under high vacuum for 12 h. The resulting yellow foam was dissolved in THF (0.1M) and cooled at −20° C. as a solution of N-chlorosuccinimide (1.2 equiv) in THF (0.3M) was added dropwise over 5 min. After stirring at −20° C. for 1 h, the mixture was poured over ice and extracted with two portions of EtOAc. The combined organic layers were washed with ice-cold brine, dried over $Na_2SO_4$, filtered and concentrated. Purification by silica gel chromatography provided (R)-5-(4-Bromo-benzyl)-7-(3,5-dichloro-phenyl)-5-methyl-6-oxo-6,7-dihydro-5H-imidazo[1,2-a]imidazole-3-sulfonyl chloride as a solid.

Example 2

(S)-2-[(R)-5-[4-(4-amino-pyrimidin-5-yl)-benzyl]-7-(3,5-dichloro-phenyl)-5-methyl-6-oxo-6,7-dihydro-5H-imidazo[1,2-a]imidazole-3-sulfonylamino]-N-(2-hydroxy-ethyl)-propionamide (660.4, M+1)

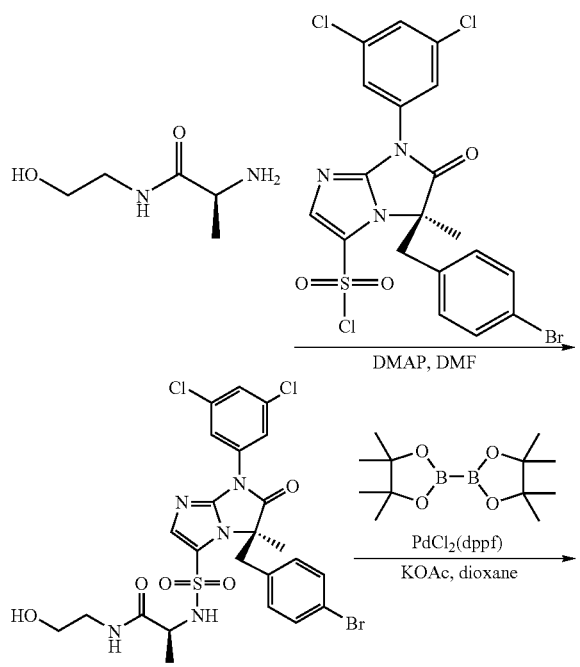

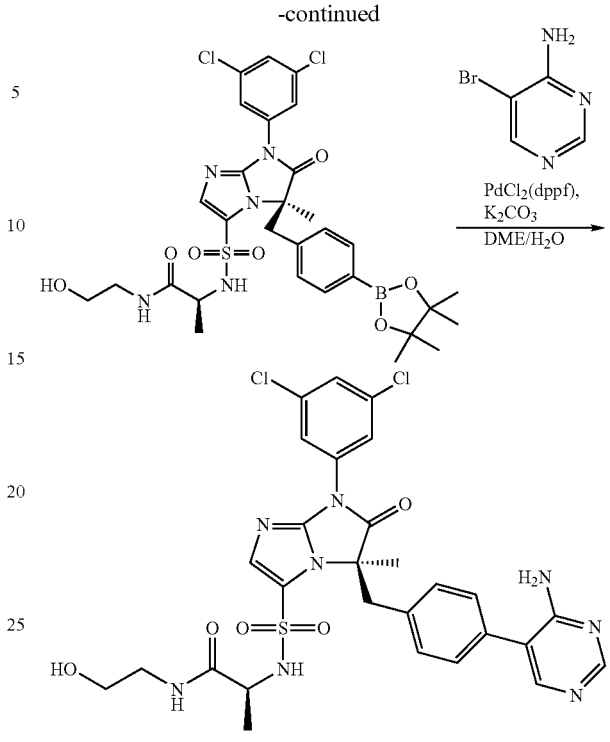

To a suspension of the hydrochloride salt of (S)-2-amino-N-(2-hydroxy-ethyl)-propionamide (0.53 g, 3.2 mmol, 3 equiv) in 10 mL of DMF was added DMAP (4 equiv), and the resulting mixture was stirred at room temp for 1 h. To this solution was added (R)-5-(4-Bromo-benzyl)-7-(3,5-dichloro-phenyl)-5-methyl-6-oxo-6,7-dihydro-5H-imidazo[1,2-a]imidazole-3-sulfonyl chloride (0.580 mg, 1.06 mmol) in 2 mL of DMF at room temp. After stirring at room temp for 15 min, the mixture was dissolved in EtOAc and washed with dilute water, HCl, saturated NaHCO3, and brine, dried over $Na_2SO_4$, filtered and concentrated. Purification of the crude product by silica gel chromatography gave 0.305 mf of the desired product.

A mixture of (S)-2-[(R)-5-(4-bromo-benzyl)-7-(3,5-dichloro-phenyl)-5-methyl-6-oxo-6,7-dihydro-5H-imidazo[1,2-a]imidazole-3-sulfonylamino]-N-(2-hydroxy-ethyl)-propionamide (0.310 g, 0.473 mmol), bis(pinacolato)diboron (0.240 g, 0.946 mmol), and KOAc (0.140 g, 1.419 mmol) in 29 mL of dioxane was flushed with $N_2$ for 15 min. $PdCl_2$(dppf) (0.039 g, 0.047 mmol) was added, and the reaction mixture was heated at 80° C. for 36 h. After cooling to room temperature, the mixture was concentrated, and the residue was diluted with 150 mL of EtOAc, washed with water and brine, dried over $MgSO_4$, and concentrated. The residue was purified by silica gel chromatography to give 0.204 g (62%) of the boronate.

A mixture of the above boronate (0.204 g, 0.295 mmol), 5-bromo-2-amino-pyrimidine (0.078 g, 0.443 mmol), and $K_2CO_3$ (0.122 g, 0.885 mmol) in 8 mL of dimethoxyethane and 1.2 mL of water was flushed with $N_2$ for 20 min. $PdCl_2$(dppf) (0.025 g, 0.030 mmol) was added, and the reaction mixture was heated at 80° C. for 2 h. After cooling to room temperature, the mixture was diluted with EtOAc, washed with water and brine, and concentrated. The residue was purified by silica gel chromatography and preparative TLC to afford 0.062 g (32%) of the title compound (660.4, M+1): The following compound was prepared by procedures analogous to those described in Example 2:

(S)-2-[(R)-5-[4-(4-Amino-pyrimidin-5-yl)-benzyl]-7-(3,5-dichloro-phenyl)-5-methyl-6-oxo-6,7-dihydro-5H-imidazo[1,2-a]imidazole-3-sulfonylamino]-N-(2-hydroxy-2-methyl-propyl)-propionamide (687.1, M+1)

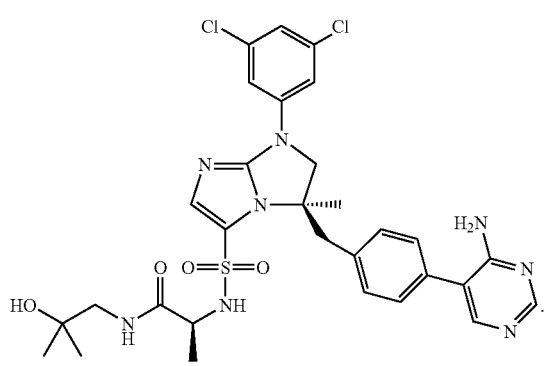

Example 3

Synthesis of (S)-2-[(R)-5-(4-cyano-benzyl)-7-(3,5-dichloro-phenyl)-5-methyl-6-oxo-6,7-dihydro-5H-imidazo[1,2-a]imidazole-3-sulfonylamino]-propionamide

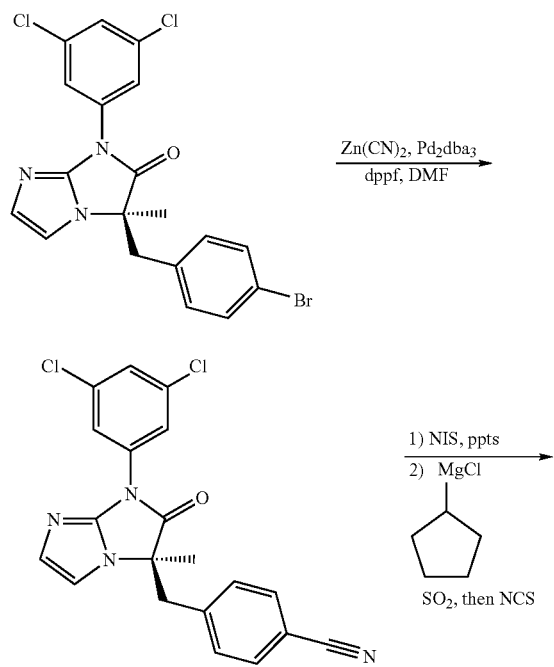

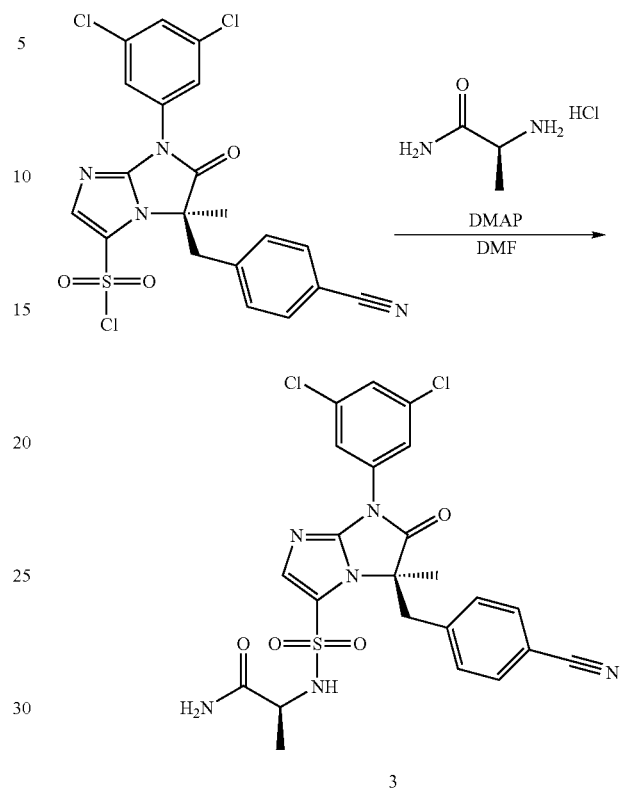

To a solution of (R)-3-(4-bromo-benzyl)-1-(3,5-dichloro-phenyl)-3-methyl-1H-imidazol-2-one (3.0 g, 6.6 mmol) in DMF (60 mL) was added Zn(CN)$_2$ (0.47 g, 4.0 mmol). The resulting solution was degassed with a strong stream of N$_2$ for 2 h. Pd$_2$dba$_3$ and dppf were added and the reaction mixture was dheated to 120° C. for 2 h. The solvent was evaporated and the residue dissolve in EtOAc, then was washed with water and brine, then was dried and filtered and the residue was purified over Florisil to afford 2.42 g of the desired product. This product was then treated in a manner similar to that described in Example 1 to produce (R)-5-(4-cyano-benzyl)-7-(3,5-dichloro-phenyl)-5-methyl-6-oxo-6,7-dihydro-5H-imidazo[1,2-a]imidazole-3-sulfonyl chloride.

L-Alaninamide hydrochloride (0.151 g, 1.209 mmol) was dissolved in anhydrous DMF and DMAP (0.197 g, 1.612 mmol) was added to the solution. The reaction mixture was stirred at room temperature for 1 h. Then, (R)-5-(4-cyano-benzyl)-7-(3,5-dichloro-phenyl)-5-methyl-6-oxo-6,7-dihydro-5H-imidazo[1,2-a]imidazole-3-sulfonyl chloride (0.24 g, 0.484 mmol) in anhydrous DMF was added to the reaction mixture and stirred for additional 10 min. The reaction solution was diluted with EtOAc and washed with water, 1 N HCl and then water. The organic phase was dried over Na$_2$SO$_4$ and concentrated under reduced pressure. The crude product was purified by silica gel column chromatography to afford 0.211 g of the title compound as a white scaly solid (M+1, 547.2).

Example 4

Synthesis of (S)-N-carbamoylmethyl-2-[(R)-5-(4-cyano-benzyl)-7-(3,5-dichloro-phenyl)-5-methyl-6-oxo-6,7-dihydro-5H-imidazo[1,2-a]imidazole-3-sulfonylamino]-propionamide

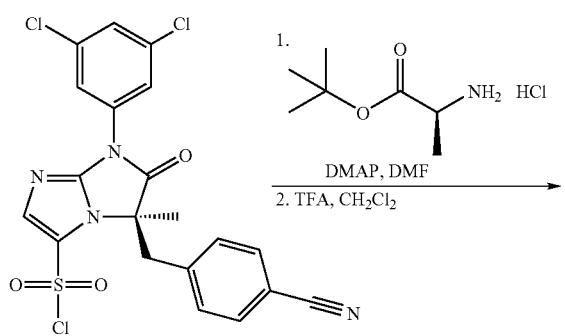

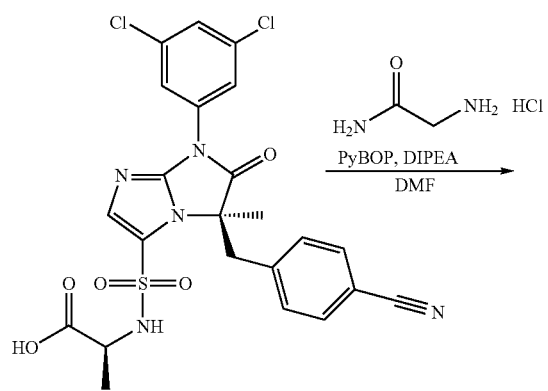

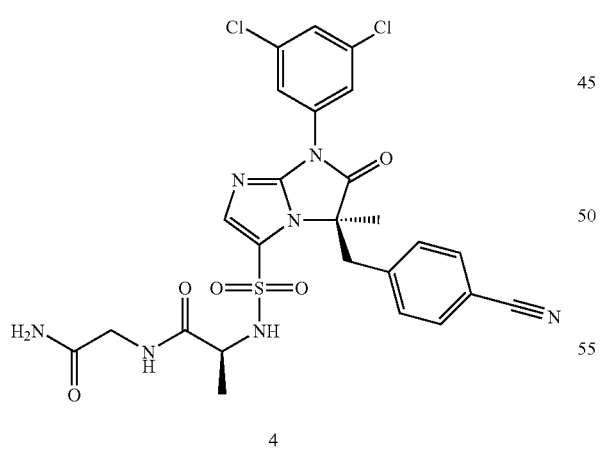

4

L-Alanine t-butyl ester hydrochloride (0.88 g, 4.84 mmol) was dissolved in anhydrous DMF (10 mL) and DMAP (0.79 g, 6.46 mmol) was added to the solution. The reaction mixture was stirred at room temperature for 1 h and (R)-5-(4-cyano-benzyl)-7-(3,5-dichloro-phenyl)-5-methyl-6-oxo-6,7-dihydro-5H-imidazo[1,2-a]imidazole-3-sulfonyl chloride (0.80 g, 1.61 mmol) in DMF was added to the reaction mixture. The reaction mixture was stirred at room temperature for another 10 min. The reaction mixture was washed with water (×3), 1N HCl and saturated NaHCO$_3$. The organic phase was dried over Na$_2$SO$_4$ and concentrated. The crude product was purified by silica gel column chromatography using CH$_2$Cl$_2$—MeOH (98:2) as an eluent to afford 0.94 g of the sulfonamide t-butyl ester. The resulting product was treated with trifluoroacetic acid (5 mL) in CH$_2$Cl$_2$ (10 mL) at room temperature for 3 h. The reaction solution was diluted with CH$_2$Cl$_2$ and washed with water. The organic phase was dried over Na$_2$SO$_4$ and then concentrated to afford 0.67 g of (S)-2-[(R)-5-(4-cyano-benzyl)-7-(3,5-dichloro-phenyl)-5-methyl-6-oxo-6,7-dihydro-5H-imidazo[1,2-a]imidazole-3-sulfonylamino]-propionic acid as a white foam.

The above carboxylic acid (0.05 g, 0.091 mmol) was dissolved in anhydrous DMF (2 mL) and benzotriazol-1-yloxytris(pyrrolidino)phosphonium hexafluorophosphate (PyBOP) (0.071 g, 0.137 mmol) was added to the reaction solution. The reaction mixture was stirred at room temperature for 10 min and glycinamide hydrochloride (0.015 g, 0.137 mmol) was added to the mixture followed by N,N-diisopropylethylamine (0.039 mL, 0.227 mmol). The reaction mixture was stirred at room temperature for another 15 min. The mixture was then diluted with EtOAc (10 mL) and washed with water (×2), 1N HCl, saturated NaHCO$_3$ and then water (×1). The organic phase was dried over Na$_2$SO$_4$ and concentrated. The crude product was purified by silica gel preparative thin layer chromatography using CH$_2$Cl$_2$—MeOH (95:5) as an eluent to afford 0.043 g of the title compound as a white foam (M+1, 604.2).

The following compound was made by procedures analogous to those described in the above example:

(S)-2-[(R)-5-(4-Cyano-benzyl)-7-(3,5-dichloro-phenyl)-5-methyl-6-oxo-6,7-dihydro-5H-imidazo[1,2-a]imidazole-3-sulfonylamino]-N-(2-hydroxy-2-methyl-propyl)-propionamide: (M+1, 619)

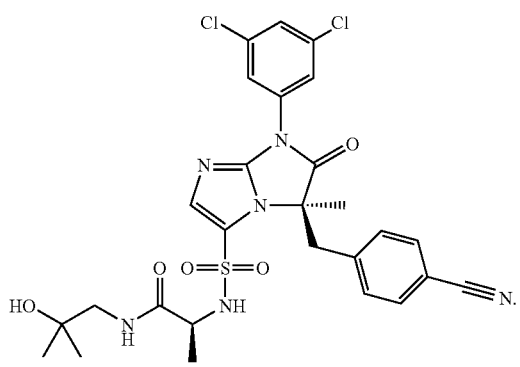

Example 5

Synthesis of (S)-N-((R)-1-carbamoyl-ethyl)-2-[(R)-5-(4-cyano-benzyl)-7-(3,5-dichloro-phenyl)-5-methyl-6-oxo-6,7-dihydro-5H-imidazo[1,2-a]imidazole-3-sulfonylamino]-propionamide

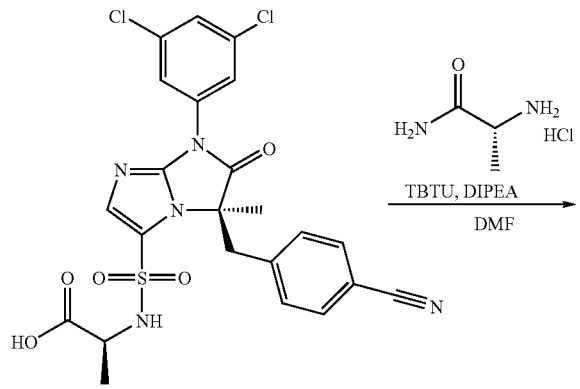

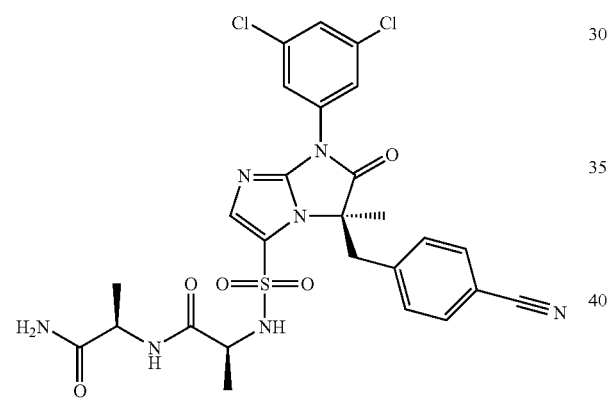

5

(S)-2-[(R)-5-(4-Cyano-benzyl)-7-(3,5-dichloro-phenyl)-5-methyl-6-oxo-6,7-dihydro-5H-imidazo[1,2-a]imidazole-3-sulfonylamino]-propionic acid (see Example 14) (0.05 g, 0.091 mmol) was dissolved in anhydrous DMF (2 mL) and TBTU (0.044 g, 0.137 mmol) was added to the reaction solution. The reaction mixture was stirred at room temperature for 10 min and D-alaninamide hydrochloride (0.017 g, 0.137 mmol) was added to the mixture followed by N,N-diisopropylethylamine (0.039 mL, 0.227 mmol). The reaction mixture was stirred at room temperature for another 15 min. The mixture was then diluted with EtOAc (10 mL) and washed with water, 1 N HCl, saturated NaHCO₃ and then water. The organic phase was dried over Na₂SO₄ and concentrated. The crude product was purified by silica gel preparative thin layer chromatography to afford 0.035 g of the title compound as a white foam (M+1, 618.2).

Example 6

(S)-2-[(R)-5-(4-cyano-benzyl)-7-(3,5-dichloro-phenyl)-5-methyl-6-oxo-6,7-dihydro-5H-imidazo[1,2-a]imidazole-3-sulfonylamino]-N-(2-hydroxy-ethyl)-propionamide

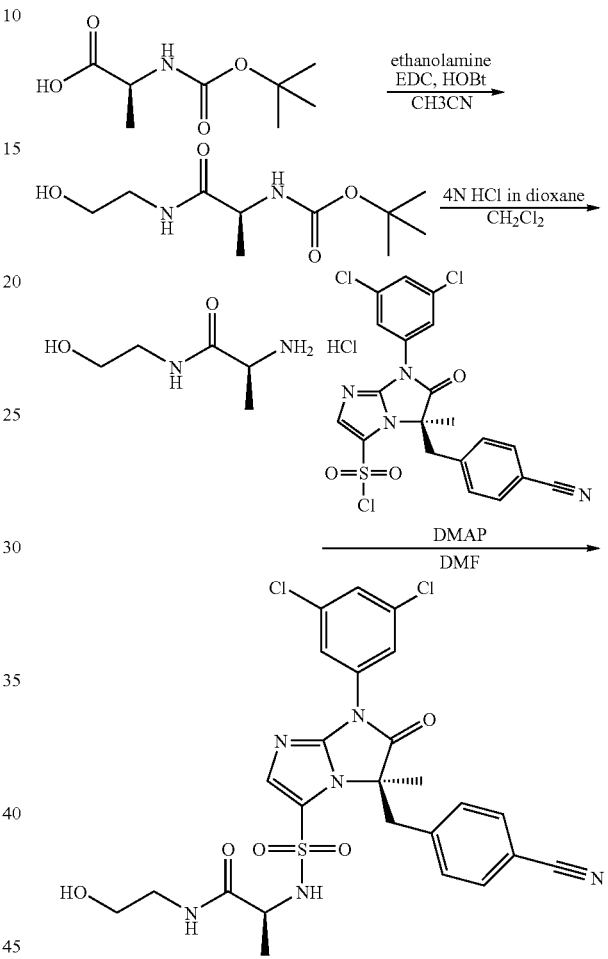

6

A mixture of L-Boc-alanine (0.40 g, 2.11 mmol), ethanolamine (0.15 mL, 2.54 mmol) and HOBt (0.29 g, 2.11 mmol) in anhydrous CH₃CN (9 mL) was cooled to 0° C. and 1-(3-dimethylaminopropyl)-3-ethylcarbodiimide hydrochloride (EDC) (0.49 g, 2.54 mmol) was added to the reaction mixture. The reaction mixture was allowed to warm to room temperature and stirred for 19 h. The reaction mixture was diluted with EtOAc and washed with 5% citric acid. The aqueous layer was extracted with EtOAc. The combined organic phases were washed with saturated NaHCO₃ and brine. The organic phase was dried over Na₂SO₄ and concentrated to afford 0.38 g of the coupled product as a colorless oil.

The above alcohol (0.34 g, 1.45 mmol) was dissolved in CH₂Cl₂ (3 mL) and 4 N HCl in dioxane (3 ml) was added to the solution. The reaction solution was stirred at room temperature for 2 h and then concentrated to afford (S)-2-amino-N-(2-hydroxy-ethyl)-propionamide hydrochloride.

To a solution of above amine salt (0.043 g, 0.254 mmol) in anhydrous DMF, was added DMAP (0.037 g, 0.303 mmol). The reaction mixture was stirred at room temperature for 1 h. (R)-5-(4-cyano-benzyl)-7-(3,5-dichloro-phenyl)-5-methyl-6-oxo-6,7-dihydro-5H-imidazo[1,2-a]imidazole-3-sulfonyl chloride (0.036 g, 0.073 mmol) was then added to the reaction mixture and stirred for another 2 h. The reaction mixture was diluted with EtOAc and washed with 1 N HCl and saturated NaHCO$_3$. The organic phase was dried over Na$_2$SO$_4$ and concentrated. The residue was purified by silica gel preparative thin layer chromatography to afford 0.035 g of the title compound as a white foam (M+1, 591.1).

Example 7

(S)-2-[(R)-5-(4-cyano-benzyl)-7-(3,5-dichloro-phenyl)-5-methyl-6-oxo-6,7-dihydro-5H-imidazo[1,2-a]imidazole-3-sulfonylamino]-5-morpholin-4-yl-5-oxo-pentanoic acid amide

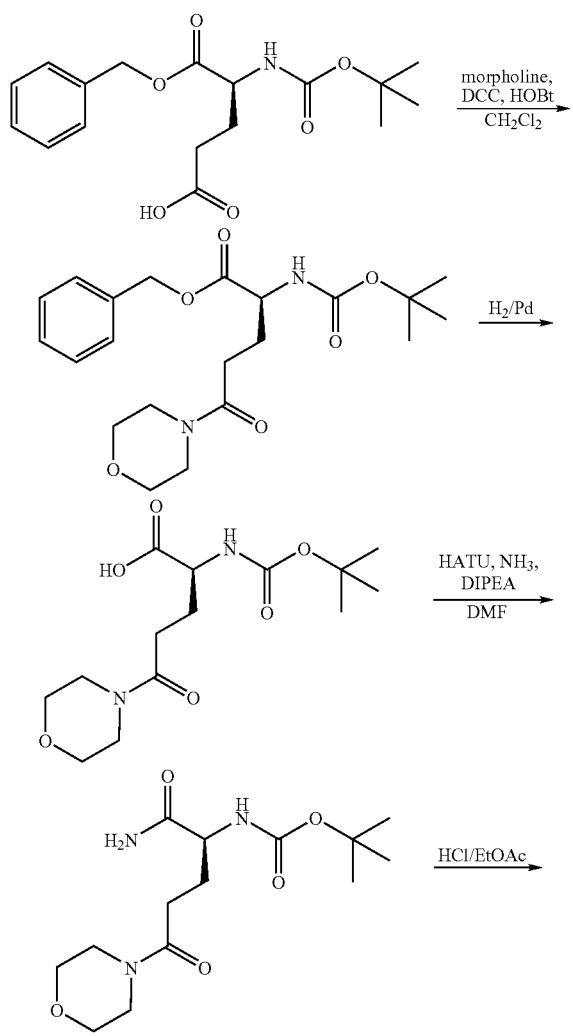

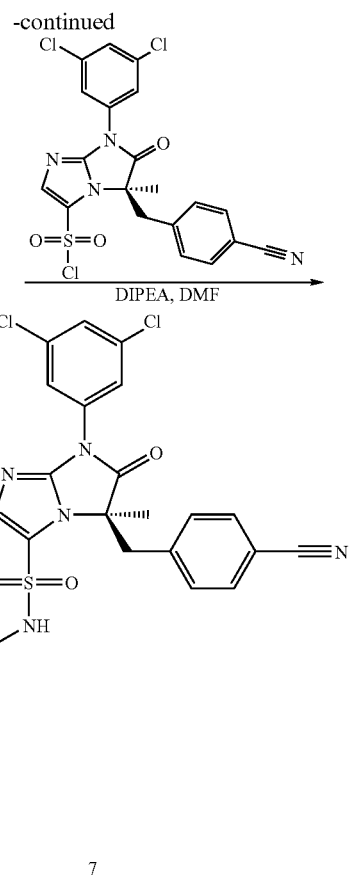

7

To a mixture of (S)-2-tert-butoxycarbonylamino-pentanedioic acid 1-benzyl ester (4.5 g, 13.4 mmol), morpholine (1.29 mL, 14.8 mmol), HOBt (1.89 g, 14.0 mmol) in CH$_2$Cl$_2$ (18 mL) at 0° C. was slowly added a solution of DCC (2.89 g, 14.0 mmol) in CH$_2$Cl$_2$ (18 mL). The resulting mixture was allowed to warm to room temperature and was stirred overnight. The resulting precipitate was filtered off and then the filtrate was diluted with CH$_2$Cl$_2$. The solution was washed with saturated NaHCO$_3$, 1 N HCl, and finally brine. The organic layer was dried over Na$_2$SO$_4$ and then filtered. Evaporation of the solvent afforded the desired amide (5.42 g) as a white solid.

A mixture of the above amide (6.17 g, 152 mmol) and 10% Pd/C (0.52 g) in EtOAc (50 mL) was hydrogenated under atmospheric pressure for 24 h. The mixture was filtered and concentrated to provide (S)-2-tert-butoxycarbonylamino-5-morpholin-4-yl-5-oxo-pentanoic acid (3.12 g) as a foam which was used without further purification.

Ammonia gas was bubbled into a solution of the carboxylic acid obtained above (3.12 g, 9.86 mmol) and O-(7-azabenzotriazol-1-yl)-N,N,N',N',-tetramethyluronium hexafluorophosphate (HATU) (5.25 g, 13.8 mmol) in DMF (30 mL) with stirring for 20 minutes. To the resulting yellow suspension was added N,N-diisopropylethylamine (5.15 mL, 29.5 mmol) via syringe. The mixture was stirred under a nitrogen atmosphere overnight. The reaction was filtered and concentrated under vacuum. The resulting residue was dissolved in CH$_2$Cl$_2$, was washed with saturated NaHCO$_3$, 1 N HCl and finally brine. The organic layer was dried over Na$_2$SO$_4$, filtered and concentrated. The resulting residue was recrystallized from EtOAc to provide the amide (1.16 g) as white solid.

The Boc group was removed with HCl in EtOAc and the resulting (S)-2-amino-5-morpholin-4-yl-5-oxo-pentanoic acid amide hydrochloride was collected by vacuum filtration and used without further purification. To a stirred solution of (R)-5-(4-cyano-benzyl)-7-(3,5-dichloro-phenyl)-5-methyl-6-oxo-6,7-dihydro-5H-imidazo[1,2-a]imidazole-3-sulfonyl chloride (76 mg, 0.13 mmol) in DMF (4 mL) was added N,N-diisopropylethylamine (60 μL, 0.39 mmol) and the amine hydrochloride (100 mg, 0.4 mmol). After stirring overnight the DMF was removed under vacuum and the resulting residue was chromatographed over silica gel. The product was then purified by semi-preparative HPLC to provide 32 mg of the title compound as a white solid (M+1, 674.04).

Example 8

Synthesis of (S)-2-[(R)-7-(3,5-dichloro-phenyl)-5-methyl-6-oxo-5-(4-trifluoromethoxy-benzyl)-6,7-dihydro-5H-imidazo[1,2-a]imidazole-3-sulfonylamino]-propionamide

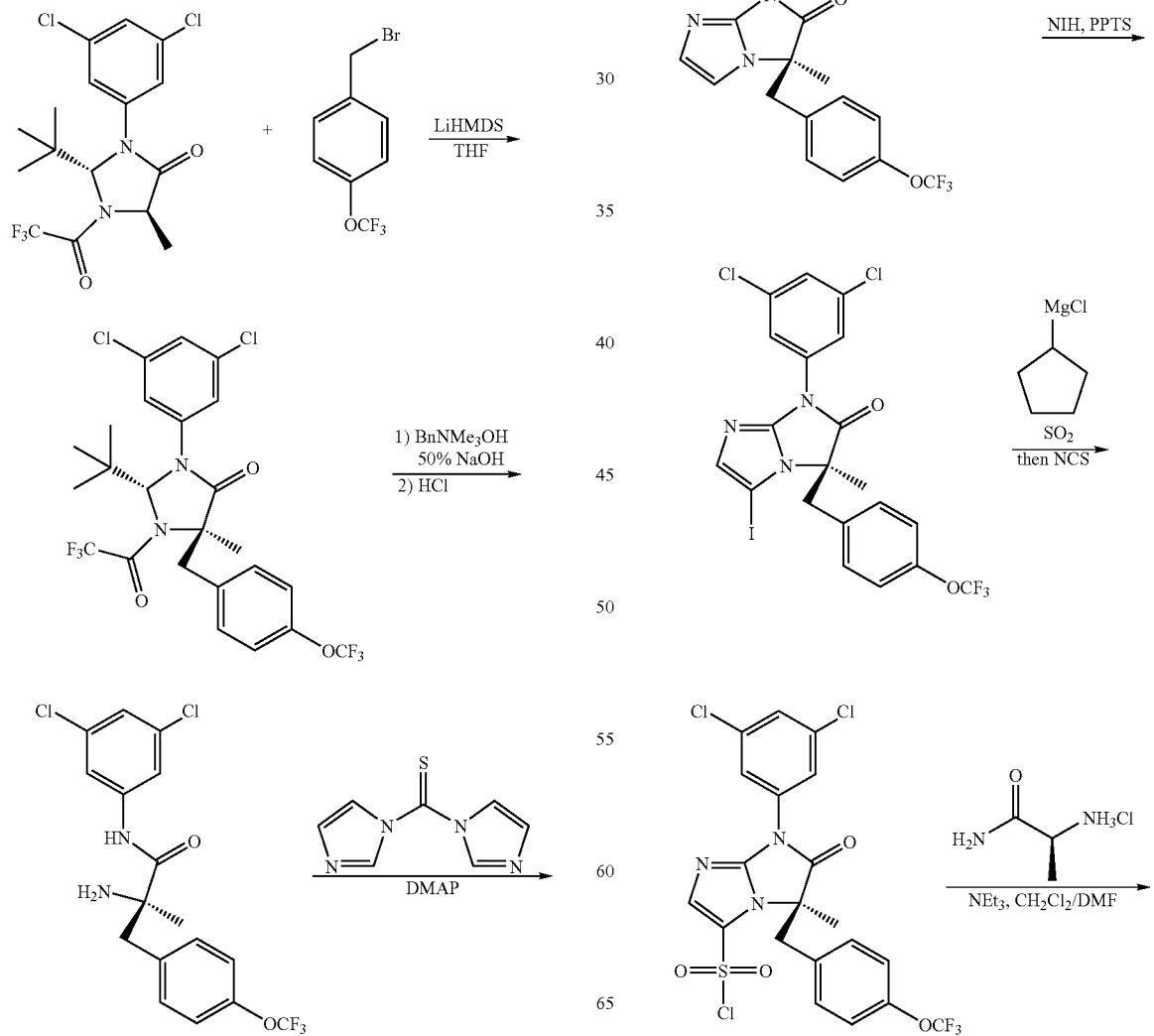

-continued

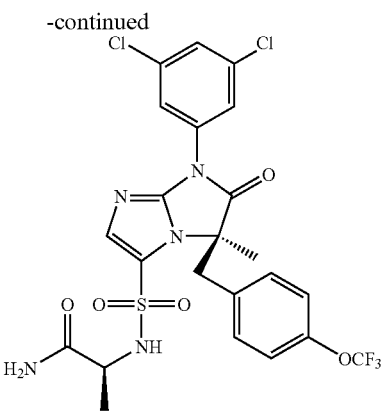

8

Lithium bis(trimethylsilyl)amide (LiHMDS) (38.0 mL, 1 M in THF) was added slowly dropwise over 25 min to a solution of (2S,5R)-2-tert-butyl-3-(3,5-dichloro-phenyl)-5-methyl-1-(2,2,2-trifluoro-acetyl)-imidazolidin-4-one (10.0 g, 25.17 mmol) in 60 mL of THF at −20° C. After stirring at −20° C. for 20 min, a solution of 4-trifluoromethoxybenzyl bromide (6.04 mL, 37.76 mmol) in 30 mL of THF was added dropwise over 20 min. The mixture was stirred at −20° C. for 45 min, warmed to −5° C. over 1 h, and then poured over 50 mL of ice-cold saturated $NH_4Cl$ solution. The resulting mixture was extracted with EtOAc. The combined organic phases were washed with brine, dried over $Na_2SO_4$, filtered and concentrated. The crude product was triturated with hexanes to afford 12.5 g (87%) of (2R,5R)-2-tert-butyl-3-(3,5-dichloro-phenyl)-5-methyl-1-(2,2,2-trifluoro-acetyl)-5-(4-trifluoromethoxy-benzyl)-imidazolidin-4-one as an off-white solid.

To a solution of the above imidazolidinone (6.0 g, 10.5 mmol) in 40 mL of dioxane was added 40% aqueous benzyltrimethylammonium hydroxide (6.59 g, 15.75 mmol) at room temperature. As the mixture was warmed to 40° C., 50% aqueous sodium hydroxide (1.68 g, 21.0 mmol) was added slowly dropwise over 5 min. The mixture was stirred at 40° C. for 18 h, then a solution of 6.4 g of conc HCl in 3.3 mL of water was added slowly dropwise over 10 min. The mixture was warmed to 50° C. and stirred for an additional 5 h, then cooled to room temperature and concentrated. 50 mL of toluene was added to the residue, and the biphasic mixture was stirred vigorously as 50% aqueous sodium hydroxide (3.0 g) was added slowly dropwise (pH of the aqueous phase≧10). The aqueous layer was extracted with toluene, and the combined organic phases were washed with water and brine, dried over $Na_2SO_4$, filtered and concentrated to afford 4.24 g of (R)-2-amino-N-(3,5-dichloro-phenyl)-2-methyl-3-(4-trifluoromethoxy-phenyl)-propionamide as a light brown oil.

To a solution of the above propionamide (4.24 g, 10.41 mmol) in 30 mL of THF was added thiocarbonyldiimidazole (2.81 g, 15.77 mmol) and 4-dimethylaminopyridine (DMAP) (0.127 g, 1.04 mmol). The mixture was heated at reflux for 17 h, cooled to room temperature and concentrated. The orange oily residue was dissolved in 50 mL of toluene and treated slowly dropwise with 20 mL of 5% aqueous HCl solution. After stirring the mixture for 10 min, the aqueous layer was separated and extracted with toluene. The combined organic phases were washed with water and brine, dried over $Na_2SO_4$, filtered and concentrated to provide 4.48 g of (R)-3-(3,5-dichloro-phenyl)-5-methyl-2-thioxo-5-(4-trifluoromethoxy-benzyl)-imidazolidin-4-one as an orange foam.

To a solution of the above thiohydantoin (4.47 g, 9.95 mmol) and aminoacetaldehyde dimethylacetal (6.50 mL, 59.7 mmol) in 20 mL of MeOH was added 7.69 mL (59.7 mmol, 70% in water) of t-butyl hydroperoxide solution, dropwise over 25 min. During the addition and for about 1 h after, the internal temperature of the mixture was kept below 20° C. with an ice water bath. The mixture was stirred at room temperature for 86 h, and 25 mL of saturated $NaHSO_3$ solution was added slowly dropwise, maintaining the internal temperature below 20° C. with an ice water bath. The resulting cloudy white mixture was concentrated. To the residue was added EtOAc, and this mixture was concentrated again. The oily residue was partitioned between EtOAc and water, and the aqueous phase was separated and extracted with EtOAc. The combined organic layers were washed with water and brine, dried over $Na_2SO_4$, filtered and concentrated to give 5.21 g of (R)-3-(3,5-dichloro-phenyl)-2-[(E)-2,2-dimethoxy-ethylimino]-5-methyl-5-(4-trifluoromethoxy-benzyl)-imidazolidin-4-one as a thick yellow oil.

A solution of the above crude acetal (5.20 g, 9.95 mmol) in 30 mL of acetone was treated with p-toluenesulfonic acid (1.89 g, 9.96 mmol). The mixture was heated at reflux for 2 h, then cooled to room temperature and concentrated. The resulting dark orange oil was dissolved in 40 mL of EtOAc and treated carefully with a solution of 2.3 g of $NaHCO_3$ in 23 mL of water. After gas evolution ceased, the aqueous phase was separated and extracted with two portions of EtOAc. The combined organic layers were washed with saturated $NaHCO_3$ solution, two portions of water, and brine, dried over $Na_2SO_4$, filtered and concentrated. The oily residue was purified by silica gel chromatography to afford 1.58 g of (R)-1-(3,5-dichloro-phenyl)-3-methyl-3-(4-trifluoromethoxy-benzyl)-1H-imidazo[1,2-a]imidazol-2-one (456.2, M+1).

A solution of (R)-1-(3,5-dichloro-phenyl)-3-methyl-3-(4-trifluoromethoxy-benzyl)-1H-imidazo[1,2-a]imidazol-2-one (Example 1) (1.54 g, 3.38 mmol) in 30 mL of THF was treated with N-iodosuccinimide (0.846 g, 3.76 mmol) and pyridinium p-toluenesulfonate (0.086 g, 3.76 mmol). The mixture was stirred at room temperature for 17 h, then diluted with EtOAc and washed with 10% $Na_2S_2O_3$ solution and water. The combined aqueous layers were extracted with 10 mL of EtOAc. The combined organic phases were washed with 25 mL of brine, dried over $Na_2SO_4$, filtered and concentrated. The crude orange oil was purified by silica gel chromatography to provide 1.27 g (65%) of (R)-1-(3,5-dichloro-phenyl)-5-iodo-3-methyl-3-(4-trifluoromethoxy-benzyl)-1H-imidazo[1,2-a]imidazol-2-one as an off-white oil (582.0, M+1).

A solution of the above iodide (1.24 g, 2.13 mmol) in 16 mL of THF was cooled at −40° C. as cyclopentyl magnesium chloride (1.17 mL, 2 M in diethyl ether) was added dropwise over 10 min. After stirring at −40° C. for 1 h, $SO_2$ (g) was added by placing an inlet needle just above the surface of the reaction mixture for 1.5 min. The bright yellow mixture was warmed to −20° C. over 1 h and then stirred at room temperature for 1 h. $N_2$ (g) was bubbled through the mixture for 20 min followed by concentration and pumping under high vacuum for 12 h. The resulting yellow foam was dissolved in 16 mL of THF and cooled at −20° C. as a solution of N-chlorosuccinimide (0.341 g, 2.56 mmol) in 8 mL of THF was added dropwise over 5 min. After stirring at −20° C. for 1 h, the mixture was poured over ice and extracted with two portions of EtOAc. The combined organic layers were washed with ice-cold brine, dried over Na₂SO₄, filtered and concentrated. Purification by silica gel chromatography provided 0.975 g (83%) of (R)-7-(3,5-dichloro-phenyl)-5-methyl-6-oxo-5-(4-trifluoromethoxy-benzyl)-6,7-dihydro-5H-imidazo[1,2-a]imidazole-3-sulfonyl chloride thick oil (554.2, M+1).

A solution of L-alaninamide HCl salt (0.097 g, 0.782 mmol) in 6.5 mL of DMF was treated with triethylamine (0.163 mL, 1.17 mmol) at room temperature. After stirring for 10 min, a solution of the above sulfonyl chloride (0.217 g, 0.391 mmol) in 1 mL of CH₂Cl₂ was added rapidly dropwise, and the cloudy mixture was stirred at room temperature for 5 h. Following the addition of EtOAc, the organic layer was washed with water, then brine, dried over Na₂SO₄, filtered and concentrated. The crude product was purified by silica gel chromatography to afford 0.193 g (81%) of the title compound as a white solid (606.3, M+1).

The following compound was prepared by a procedure analogous to Example 8:

(R)-2-[(R)-7-(3,5-Dichloro-phenyl)-5-methyl-6-oxo-5-(4-trifluoromethoxy-benzyl)-6,7-dihydro-5H-imidazo[1,2-a]imidazole-3-sulfonylamino]-propionamide (606.4, M+1):

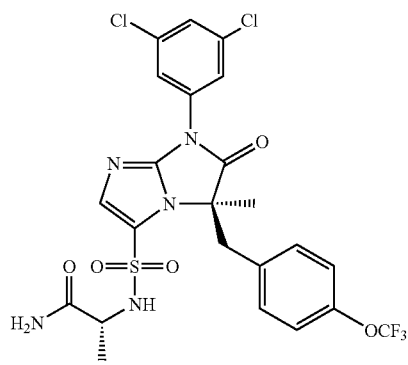

Example 9

Synthesis of (S)-2-[(R)-7-(3,5-dichloro-phenyl)-5-methyl-6-oxo-5-(4-trifluoromethoxy-benzyl)-6,7-dihydro-5H-imidazo[1,2-a]imidazole-3-sulfonylamino]-N-(2-hydroxy-ethyl)-propionamide

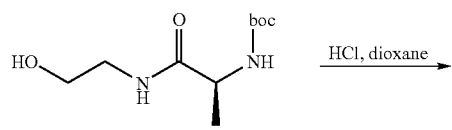

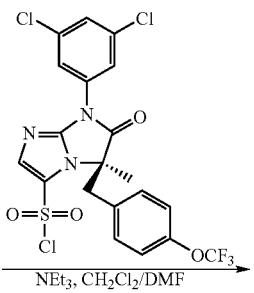

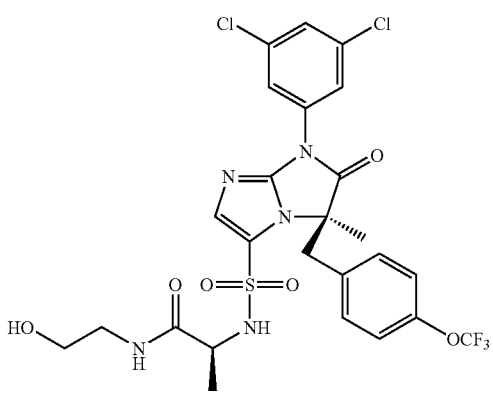

To a suspension of N-Boc-L-(N-hydroxyethyl)alaninamide (0.188 g, 0.809 mmol) in 1 mL of dioxane was added HCl (2.0 mL, 4 M in dioxane), and the resulting cloudy mixture was stirred at room temperature for 2.5 h. Concentration of the mixture was followed by addition of CH₂Cl₂, and this process was repeated twice. Final pumping under high vacuum for 12 h afforded a colorless oil. The crude amine HCl salt was dissolved in 1.5 mL of DMF and treated with triethylamine (0.157 mL, 1.13 mmol). After stirring at room temperature for 10 min, a solution of (R)-7-(3,5-dichloro-phenyl)-5-methyl-6-oxo-5-(4-trifluoromethoxy-benzyl)-6,7-dihydro-5H-imidazo[1,2-a]imidazole-3-sulfonyl chloride (0.125 g, 0.225 mmol) in 3 mL of CH₂Cl₂ was added rapidly dropwise via cannula. The reaction mixture was stirred at room temperature for 4 h. Following the addition of EtOAc, the organic layer was washed with three portions of 5% NaCl solution, then brine, dried over Na₂SO₄, filtered and concentrated. The crude product was purified by preparative TLC to afford 0.118 g (81%) of the title compound as a white foam (649.9, M+1).

The following compound was prepared by a procedure analogous to Example 9:

(S)-2-[(R)-7-(3,5-Dichloro-phenyl)-5-methyl-6-oxo-5-(4-trifluoromethoxy-benzyl)-6,7-dihydro-5H-imidazo[1,2-a]imidazole-3-sulfonylamino]-N-(2-hydroxy-2-methyl-propyl)-propionamide (678.3, M+1)

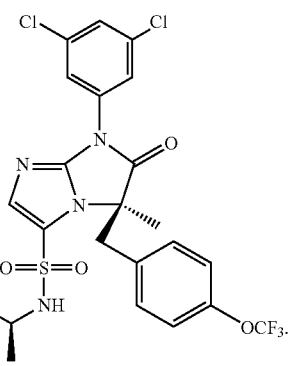

Description of Biological Properties

The biological properties of representative compounds of the formula I were investigated by way of the experimental protocol described below.

Assay to Determine Inhibition of LFA-1 Binding to ICAM-1

Purpose of Assay:

This assay protocol is designed to study the direct antagonism, by a test compound, of the interaction of the CAM, ICAM-1 with the Leukointegrin CD18/CD11a (LFA-1).

Description of Assay Protocol:

LFA-1 is immunopurified using the TS2/4 antibody from a 20 g pellet of human JY or SKW3 cells, utilizing a protocol previously described (Dustin, M. J.; et al., *J. Immunol.* 1992, 148, 2654-2660). The LFA-1 is purified from SKW3 lysates by immunoaffinity chromatography on TS2/4 LFA-1 mAb Sepharose and eluted at pH 11.5 in the presence of 2 mM $MgCl_2$ and 1% octylglucoside. After collection and neutralization of fractions from the TS2/4 column, samples are pooled and precleared with Protein G agarose.

A soluble form of ICAM-1 is constructed, expressed, purified and characterized as previously described (Marlin, S.; et al., *Nature,* 1990, 344, 70-72 and see Arruda, A.; et al., *Antimicrob. Agents Chemother.* 1992, 36, 1186-1192). Briefly, isoleucine 454 which is located at the putative boundary between domain 5 of the ectodomain and the transmembrane domain, is changed to a stop codon using standard oligonucleotide-directed mutagenesis. This construction yields a molecule identical with the first 453 amino acids of membrane bound ICAM-1. An expression vector is created with a hamster dihydrofolate reductase gene, a neomycin-resistance marker, and the coding region of the sICAM-1 construct described above, along with the promoter, splice signals, and polyadenylation signal of the SV40 early region. The recombinant plasmid is transfected into CHO DUX cells using standard calcium phosphate methods. Cells are passaged in selective media (G418) and colonies secreting sICAM-1 are amplified using methotrexate. sICAM-1 is purified from serum-free media using traditional non-affinity chromatographic techniques, including ion exchange and size exclusion chromatography.

LFA-1 binding to ICAM-1 is monitored by first incubating sICAM-1 at 40 µg/mL in Dulbecco's phosphate buffered saline with calcium and magnesium, additional 2 mM $MgCl_2$ and 0.1 mM PMSF (Diluting Buffer) in a 96-well plate for 30 min at room temperature. Plates are then blocked by the addition of 2% (w/v) bovine serum albumin in Diluting Buffer for 37° C. for 1 h. Blocking solution is removed from wells, and test compounds are diluted and then added followed by the addition of approximately 25 ng of immunoaffinity purified LFA-1. The LFA-1 is incubated in the presence of test compound and ICAM-1 at 37° C. for 1 h. Wells are washed 3 times with Diluting Buffer. The bound LFA-1 is detected by the addition of a polyclonal antibody directed against a peptide corresponding to the CD18 cytoplasmic tail in a 1:100 dilution with Diluting Buffer and 1% BSA and allowed to incubate for 45 min at 37° C. Wells are washed 3 times with Diluting Buffer and the bound polyclonal antibody is detected by the addition of a 1:4000 dilution of horse radish peroxidase conjugated to goat immunoglobulin directed against rabbit immunoglobulin. This reagent is allowed to incubate for 20 min at 37° C., wells are washed as above and the substrate for the horse radish peroxidase is added to each well to develop a quantitative colorimetric signal proportional to the amount of LFA-1 bound to sICAM-1. Soluble ICAM-1 (60 µg/mL) is used as a positive control for inhibition of the LFA-1/ICAM-1 interaction. The lack of the addition of LFA-1 to the binding assay is used as a background control for all samples. A dose-response curve is obtained for all test compounds.

All compounds made in the above examples were tested in this assay and each found to have a $K_d$<10 µM.

Assay to Determine Metabolism by Human Liver Microsomal Enzymes

Purpose of Assay:

This assay protocol is designed to measure the in vitro metabolism of test compounds by human liver microsomal enzymes. The data collected are analyzed to calculate a half-life ($t_{1/2}$, min) for test compounds.

Description of Assay Protocol:

The assay is performed in 50 mM potassium phosphate buffer, pH 7.4 and 2.5 mM NADPH. Test samples are dissolved in acetonitrile for a final assay concentration of 1-10 µM. Human liver microsomes are diluted in assay buffer to a final assay concentration of 1 mg protein/mL. A volume of 25 µL compound solution and 50 µL microsome suspension are added to 825 µL assay buffer. The preparation is incubated for 5 min in a 37° C. water bath. The reaction is started by the addition of 100 µL NADPH. Volumes of 80 µL are removed from the incubation mix at 0, 3, 6, 10, 15, 20, 40, and 60 min after the start of the reaction and added to 160 µL acetonitrile. The samples are shaken for 20 sec and then centrifuged for 3 min at 3000 rpm. A 200 µL volume of the supernatant is transferred to 0.25 mm glass fiber filter plates and centrifuged for 5 min at 3000 rpm. Injection volumes of 10 µL are typically added to Zorbax SB C8 HPLC columns with formic acid in water or acetonitrile at a flow rate of 1.5 mL/min. Percent loss of parent compound is calculated from the area under each time point to determine the half-life.

Compounds made in the above examples were tested in this assay and generally found to have a $t_{1/2} \geq 50$ minutes.

Description of Therapeutic Use

The novel small molecules of formula I provided by the invention inhibit the ICAM-1/LFA-1 dependent homotypic aggregation of human lymphocytes and human lymphocyte adherence to ICAM-1. These compounds have therapeutic utility in the modulation of immune cell activation/proliferation, e.g., as competitive inhibitors of intercellular ligand/receptor binding reactions involving CAMs and Leukointegrins. To be more specific, the compounds of the invention may be used to treat certain inflammatory conditions, including conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The compounds of the invention may also be used in treating asthma or as an adjunct to minimize toxicity with cytokine therapy in the treatment of cancers. In general these compounds may be employed in the treatment of those diseases currently treatable through steroid therapy.

Thus, another aspect of the invention is the provision of a method for the treatment or prophylaxis of the above-described conditions through the adminstration of therapeutic or prophylactic amounts of one or more compounds of the formula I.

In accordance with the method provided by the invention, the novel compounds of formula I may be administered for either a prophylactic or therapeutic purpose either alone or with other immunosuppressive or antiinflammatory agents. When provided prophylactically, the immunosuppressive compound(s) are provided in advance of any inflammatory response or symptom (for example, prior to, at, or shortly after the time of an organ or tissue transplant but in advance of any symptoms of organ rejection). The prophylactic administration of a compound of the formula I serves to prevent or attenuate any subsequent inflammatory response (such as, for example, rejection of a transplanted organ or tissue, etc.). The therapeutic administration of a compound of the formula I serves to attenuate any actual inflammation (such as, for example, the rejection of a transplanted organ or tissue). Thus, in accordance with the invention, a compound of the formula I can be administered either prior to the onset of inflammation (so as to suppress an anticipated inflammation) or after the initiation of inflammation.

The novel compounds of the formula I may, in accordance with the invention, be administered in single or divided doses by the oral, parenteral or topical routes. A suitable oral dosage for a compound of formula I would be in the range of about 0.1 mg to 10 g per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered topically or by suppository.

FORMULATIONS

Compounds of the formula I can be formulated for therapeutic administration in a number of ways. Descriptions of several exemplary formulations are given below.

Example A

Capsules or Tablets

| Example A-1 | | Example A-2 | |
| --- | --- | --- | --- |
| Ingredients | Quantity | Ingredients | Quantity |
| Compound of formula I | 250 mg | Compound of formula I | 50 mg |
| Starch | 160 mg | Dicalcium Phosphate | 160 mg |
| Microcrys. Cellulose | 90 mg | Microcrys. Cellulose | 90 mg |
| Sodium Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of formula I is blended into a powder mixture with the premixed excipient materials as identified above with the exception of the lubricant. The lubricant is then blended in and the resulting blend compressed into tablets or filled into hard gelatin capsules.

Example B

Parenteral Solutions

| Ingredients | Quantity |
| --- | --- |
| Compound of formula I | 500 mg |
| PEG 400 | 40% by volume |
| Ethyl Alcohol | 5% by volume |
| Saline | 55% by volume |

The excipient materials are mixed and then added to one of the compounds of formula I in such volume as is necessary for dissolution. Mixing is continued until the solution is clear. The solution then filtered into the appropriate vials or ampoules and sterilized by autoclaving.

Example C

Suspension

| Ingredients | Quantity |
| --- | --- |
| Compound of formula I | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water and thereafter one of the compounds of formula I is added and mixing is continued until the suspension is homogeneous. The suspension is then transferred into the appropriate vials or ampoules.

Example D

Topical Formulation

| Ingredients | Quantity |
| --- | --- |
| Compound of formula I | 5% by weight |
| Tefose 63 | 13% by weight |
| Labrafil M 1944 CS | 3% by weight |
| Paraffin Oil | 8% by weight |
| Methylparaben (MP) | 0.15% by weight |
| Propylparaben (PP) | 0.05% by weight |
| Deionized water | q.s. to 100 |

The proper amounts of Tefose 63, Labrafil M 1944 CS, Paraffin oil and water are mixed and heated at 75° C. until all components have melted. The mixture is then cooled to 50° C. with continuous stirring. Methylparaben and propylparaben are added with mixing and the mixture is cooled to ambient temperature. The compound of formula I is added to the mixture and blended well.

What is claimed is:

1. A method for treating psoriasis in a patient which comprises administering to said patient a therapeutically effective amount of a compound of the formula I:

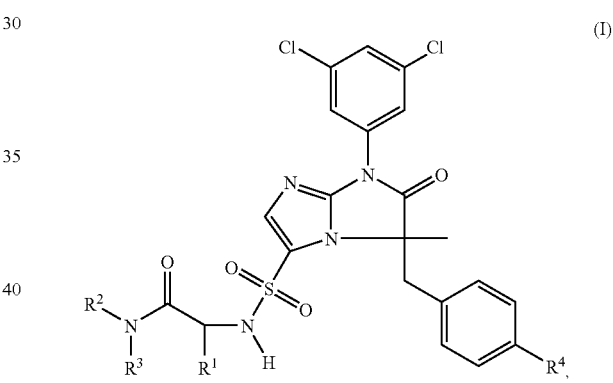

(I)

wherein:
  $R^1$ is straight or branched alkyl of 1 to 3 carbon atoms which is optionally mono- or disubstituted with oxo;
  $R^2$ and $R^3$ are each independently selected from the group consisting of:
    (A) hydrogen, and
    (B) straight or branched alkyl of 1 to 4 carbon atoms which alkyl group is mono- or disubstituted with moieties independently selected from the group consisting of:
      (i) $CONH_2$ and
      (ii) OH,
  and
  $R^4$ is:
    (A) cyano, or
    (B) trifluoromethoxy;
or a pharmaceutically acceptable salt thereof.

2. The method of claim 1, wherein:
  $R^1$ is a methyl group;
  $R^2$ and $R^3$ are each, independently selected from the group consisting of:

(A) hydrogen and
(B) straight or branched alkyl of 1 to 4 carbon atoms which is mono- or disubstituted with moieties independently selected from the group consisting of:
  (i) $CONH_2$ and
  (ii) OH; and
$R^4$ is
(A) cyano or
(B) trifluoromethoxy.

3. The method of claim 1, wherein:
$R^1$ is a methyl group;
$R^2$ and $R^3$ are each, independently selected from the group consisting of:
(A) hydrogen and
(B) straight or branched alkyl of 1 to 4 carbon atoms which is mono- or disubstituted with moieties independently selected from the group consisting of:
  (i) $CONH_2$ and
  (ii) OH; and
$R^4$ is trifluoromethoxy.

4. The method of claim 1, wherein the compound of formula (I) is selected from:
  (S)-2-[(R)-5-(4-Cyano-benzyl)-7-(3,5-dichloro-phenyl)-5-methyl-6-oxo-6,7-dihydro-5H-imidazo[1,2-a]imidazole-3-sulfonylamino]-propionamide;
  (S)-2-[(R)-7-(3,5-Dichloro-phenyl)-5-methyl-6-oxo-5-(4-trifluoromethoxy-benzyl)-6,7-dihydro-5H-imidazo[1,2-a]imidazole-3-sulfonylamino]-N-(2-hydroxy-2-methyl-propyl)-propionamide;
  (S)-2-[(R)-7-(3,5-Dichloro-phenyl)-5-methyl-6-oxo-5-(4-trifluoromethoxy-benzyl)-6,7-dihydro-5H-imidazo[1,2-a]imidazole-3-sulfonylamino]-propionamide; and
  (S)-N-Carbamoylmethyl-2-[(R)-5-(4-cyano-benzyl)-7-(3,5-dichloro-phenyl)-5-methyl-6-oxo-6,7-dihydro-5H-imidazo[1,2-a]imidazole-3-sulfonylamino]-propionamide.

* * * * *